United States Patent [19]

Noyori et al.

[11] Patent Number: 5,329,035

[45] Date of Patent: Jul. 12, 1994

[54] PROCESS FOR PRODUCING 2,3-DISUBSTITUTED-4-SUBSTITUTED CYCLOPENTANONES, ENANTIOMORPHS, OR MIXTURES THEREOF

[75] Inventors: Ryoji Noyori, Nisshin; Masaaki Suzuki, Nagoya; Toshio Tanaka, Hino; Seizi Kurozumi, Kokubunji, all of Japan

[73] Assignee: Teijin Limited, Osaka, Japan

[21] Appl. No.: 38,066

[22] Filed: Mar. 29, 1993

Related U.S. Application Data

[63] Continuation-in-part of Ser. No. 728,053, Jul. 8, 1991, which is a continuation of Ser. No. 377,751, Jul. 7, 1989, abandoned, which is a continuation of Ser. No. 231,669, Aug. 12, 1988, abandoned, which is a continuation of Ser. No. 784,598, Oct. 4, 1985, abandoned.

[30] Foreign Application Priority Data

Oct. 8, 1984 [JP] Japan .................. 59-209629
Nov. 9, 1984 [JP] Japan .................. 59-235307
Feb. 18, 1985 [JP] Japan .................. 60-028430

[51] Int. Cl.$^5$ ................. C07C 405/00; C07F 7/18
[52] U.S. Cl. ................. 556/441; 560/121; 562/503

[58] Field of Search ............... 560/121; 502/503; 556/441

[56] References Cited

FOREIGN PATENT DOCUMENTS

03063243 4/1991 Japan.

OTHER PUBLICATIONS

Rinns, Tetrahedron Letters 26 (28) 3385 (1985).
Nishiyama, Tet Letters, 25, 2487 (1984).
Noyori Ang. Chem. Int Ed. 23, 847 (1984).
Suzuki, J. A. C. S. 107, 3348 (1985).

*Primary Examiner*—Robert Gerstl
*Attorney, Agent, or Firm*—Sherman and Shalloway

[57] ABSTRACT

A process for producing a 2,3-disubstituted-4-substituted cyclopentanone, an enantiomorph thereof, or a mixture of these in an arbitrary ratio.

The process comprises (A) subjecting a 4-substituted-2-cyclopentenone, an enantiomorph thereof, or a mixture of these in an arbitrary ratio, and an organocopper compound to conjugate addition-reaction, and thereafter (B) reacting the resulting enolate intermediate with a halide in the presence of a phenyl organotin compound.

18 Claims, No Drawings

PROCESS FOR PRODUCING 2,3-DISUBSTITUTED-4-SUBSTITUTED CYCLOPENTANONES, ENANTIOMORPHS, OR MIXTURES THEREOF

This application is a continuation-in-part of application Ser. No. 07/728,053, filed Jul. 8, 1991; which is a continuation of application Ser. No. 07/377,751, filed Jul. 7, 1989, now abandoned; which is a continuation of application Ser. No. 07/231,669, filed Aug. 12, 1988, now abandoned; which is a continuation of application Ser. No. 06/784,598, filed Oct. 4, 1985, now abandoned.

This invention relates to a process for producing 2,3-disubstituted-4-substituted cyclopentanones, enantiomorphs, or mixtures thereof.

Natural prostaglandins (prostaglandin will be abbreviated hereinafter as PG) are known as local hormones (autacoid) having high biological and pharmacological activities. In an attempt to develop new medicines by skillfully utilizing these physiological characteristics of PGs, not only natural PGs but various derivatives thereof have been studied.

Natural $PGE_2$ and $PGF_2$ as typical compounds of PGE and PGFs have the activity of contracting the smooth muscles of the uterus, and are used as most useful labor inducing agents. Natural $PGE_1$, on the other hand, is a type-L prostaglandin and has unique biological activities such as platelet aggregation inhibiting activity and blood pressure lowering activity. In recent years, natural $PGE_1$ has been used as an agent for treating peripheral vascular diseases in the cardiovascular therapeutic field.

A number of methods have heretofore been known for obtaining these PGEs and PGFs [see J. B. Bindra et al.; Prostaglandin Synthesis, Academic Press (1977)]. Typical examples of such methods are listed below.

(i) Biosynthesis from arachidonic acid or di-homo-gamma-linolenic acid [see B. Samuelson et al. Angev. Chem. Int. Ed. ENgl. 4, 410 (1965)].

(ii) Synthesis via the Corey lactone which is an important key-intermediate [see E. J. Corey et al., J. Amer. Chem. Soc., 92, 397 (1970)].

(iii) Synthesis through a 2-substituted-2-cyclopentenone which is also an important intermediate [see C. J. Sih et al., J. Amer. Chem. Soc., 97, 865 (1975)].

(iv) Selective reduction of 5,6-dehydro-$PGE_2$ or $PGF_{2\alpha}$ [see E. S. Ferdinandi et al., Can. J. Chem., 49, 1070 (1971); and C. H. Lin et al., Prostaglandin, 11, 377 (1976)].

According to the biosynthetic method (i), the starting poly-unsaturated fatty acid is difficult to procure. Moreover, the yield of the desired product from this starting material is very low, and it is difficult to isolate it in pure form from the by-products. In the chemical synthetic methods (ii) to (iv), many steps are required for obtaining the starting materials. Even when the starting materials are easily available, the production of prostaglandins from them requires many steps, and the total yields of the prostaglandins are still very low. Hence, these methods are still desired to be improved.

In an attempt to overcome the various difficulties of these methods, a three-component coupling process for the synthesis of a PG skeleton was proposed which involves conjugate addition to a 2-cyclopentenone compound followed by a step of trapping the enolate [see G. Stock et al., J. Amer. Chem. Soc., 97, 6260 (1975), and K. G. Untch et al., J. Org. Chem. 44, 3755). This process, however, has the difficulty that it has to go through many steps in which formaldehyde, a low molecular compound, is used to trap the enolate and the PG skeleton is synthesized chemically through the resulting important intermediate, and that the total yield of the desired product is low.

On the other hand, the following methods have been proposed for more efficient production of the PG skeleton by the three-component coupling process.

(1) Japanese Laid-Open Patent Publications Nos. 96542/1975 and 101337/1975, G. H. Posner et al., Tetrahedron Letters, 2591 (1974), and G. H. Posner et al., J. Amer. Chem. Soc., 97, 107 (1974).

These documents disclose a method for producing 2,3-disubstituted cyclopentanones by conjugate addition of an organocopper compound to 2-cyclopentenone and subsequent alkylation of the reaction product with halides. These documents, however, fail to give a working example covering the production of prostaglandins and only describe a working example carried out in a model system. None of them disclose an example of producing 2,3-disubstituted-4-substituted cyclopentanones from 4-substituted-2-cyclopentenones.

(2) J. W. Patterson, Jr. and J. H. Fried., J. Org. Chem., 39, 2506 (1974).

The authors successfully synthesized 11-deoxyprostaglandin $E_1$ by applying the method (1) to 2-cyclopentenones. However, they do not disclose even the possibility of producing 2,3-disubstituted-4-substituted-cyclopentanones from 4-substituted-2-cyclopentenones.

(3) G. Stork and M. Isobe, J. Am. Chem. Soc., 97, 6260 (1975).

The authors succeeded in conjugate addition of an organocopper compound to a 4-substituted-2-cyclopentenone and trapping the resulting enolate by monomeric formaldehyde. But they gave a negative conclusion about the alkylation reaction of trapping the enolate with an alkylating agent.

(4) J. A. Noguez and L. A. Maldonado, Synthetic Communications, 6, 39 (1976).

According to the method disclosed in this document, a lithium salt of cyanohydrin whose part corresponding to the omega-chain of prostaglandin is protected is introduced into 2-cyclopentenone by conjugate addition, and the resulting enolate is captured by a propargyl halide to obtain a 11-deoxyprostaglandin derivative. However, it does not even disclose the possibility of producing 2,3-disubstituted-4-substituted-cyclopentanones from 4-substituted-2-cyclopentenones.

(5) R. Davis and K. G. Untch, J. Org. Chem., 44, 3755 (1979).

The authors stated that various investigations were made in an attempt to add an organocopper compound having an organic group corresponding to the omega-chain of prostaglandin to a 4-substituted-2-cyclopentenone by conjugate addition, and to alkylate the resulting enolate directly with an allyl halide, but all of the attempts were unsuccessful.

(6) A. J. Dixon and R. J. K. Taylor, J. Chem. Soc., Parkin I, 1407 (1981).

The authors challenged the allylation of an enolate formed from 2-cyclopentenone and an organocopper compound which had been considered to be difficult of proceeding, and succeeded in obtaining an intermediate for the synthesis of 11-deoxyprostaglandin. They, however, failed to disclose anything about a specific example, or even the possibility, of a process for producing 2,3-disubstituted-4-substituted cyclopentanones from 4-substituted-2-cyclopentenones.

(7) Nishiyama et al., Tetrahedron Letters, 25, 223 (1984) and 25, 2487 (1984).

The authors succeeded in introducing trimethylsilyl-lithium or methyllithiotrimethylsilyl acetate into 2-cyclopentenone by conjugate addition, adding tributyl-tin chloride, and thereafter alkylating the enolate with a propargyl bromide derivative. But they failed to disclose a specific example, or even the possibility, of a process for producing 2,3-disubstituted-4-substituted cyclopentanones from 4-substituted-2-cyclopentenones.

For the prior art techniques (1) to (7) and the other prior techniques, reference may be made to a general synthesis entitled (Prostaglandin Sytheses by Three-Component Coupling" by Ryoji Noyori et al. in Angewandte Chemie, International Edition in English, 23, No. 11, November 1984, pages 847–876.

It is an object of this invention to provide a novel process for producing 2,3-disubstituted-4-substituted cyclopentanones, enantiomorphs thereof, or mixtures thereof.

Another object of this invention is to provide a process for efficiently producing 2,3-disubstituted-4-substituted cyclopentanones such as PGEs, enantiomorphs thereof, or mixtures thereof.

Still another object of this invention is to provide a process for producing a 2,3-disubstituted-4-substituted cyclopentanone easily in high yields in one step or a single pot on the basis of the present inventors' discovery that the 2,3-disubstituted-4-substituted cyclopentanone, which cannot be produced via a lithium enolate or copper enolate in the prior art, can now be produced via a tin enolate.

A further object of this invention is to provide a novel process for producing 2,3-disubstituted-4-substituted cyclopentanones in one step or a single pot on the basis of the present inventors' discovery that when the 4-substituted-2-cyclopentenone and an organocopper compound are subjected to conjugate addition reaction and the resulting copper enolate is converted to a tin enolate in situ, the tin enolate can be directly reacted with an alkyl halide or an alkenyl halide.

Other objects and advantages of this invention will become apparent from the following description.

According to this invention, the above objects and advantages of this invention are achieved by a process for producing a 2,3-disubstituted-4-substituted cyclopentanone represented by the following formula

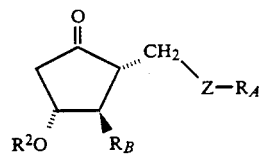 (6)

$R^2$ represents a tri($C_1$–$C_7$)hydrocarbon silyl group or $R^2O$ represents an acetal linkage, $R_B$ represents a substituted or unsubstituted $C_2$–$C_{10}$ alkyl or alkenyl group, Z represents an ethylene, ethynylene, trans-vinylene, cis-vinylene, phenylene or phenyleneoxa group, and $R_A$ represents a hydrogen atom or a substituted or unsubstituted $C_1$–$C_7$ alkyl or alkenyl group, an enantiomorph thereof, or a mixture of these in an arbitrary ratio, which comprises (A) subjecting a 4-substituted-2-cyclopentenone represented by the following formula

 (1)

wherein $R^2$ is as defined above,
an enantiomorph thereof, or a mixture of these in an arbitrary ratio, and an organocopper compound formed from an organolithium compound represented by the following formula $$R_B\text{—Li} \quad (2)$$

wherein $R_B$ is as defined above,
and a copper compound represented by the following formula $$\text{Cu—Q} \quad (3)$$

wherein Q represents a halogen atom, a cyano group, a phenylthio group or a 1-pentynyl group,
to conjugate addition-reaction, and thereafter, (B) reacting the resulting enolate intermediate with a halide represented by the following formula $$\text{X-CH}_2\text{-Z-R}_A \quad (5)$$

wherein Z and $R_A$ are as defined above, and X represents a halogen atom or a tosyl group,
in the presence of an organotin compound represented by the following formula $$R_3\text{SnY} \quad (4)$$

wherein R's are identical or different and each represents a $C_1$–$C_4$ alkyl group, a $C_3$–$C_7$ cycloalkyl group, a phenyl group or a halogen atom provided that two or three R's cannot be halogen atoms at the same time, and Y represents a halogen atom or a trifrate group, The process of this invention comprises a conjugate addition-reaction step (A) of reacting the 4-substituted-2-cyclopentenone (1), or an enantiomorph thereof, or a mixture of these, with the organocopper compound formed from the organolithium compound (2) and the copper compound (3), and the step (B) of reacting the enolate intermediate formed in step (A) with the halide (5) in the presence of the organotin compound (4).

The 4-substituted-2-cyclopentenone used as a starting material in this invention is represented by formula (1). $R^2$ in formula (1) represents a tri($C_1$–$C_7$)hydrocarbon silyl group or a group forming an acetal linkage ($OR^2$) together with the oxygen atom of the hydroxyl group.

Examples of the tri(C–$C_7$)hydrocarbon silyl group include tri($C_1$–$C_4$)alkylsilyl groups such as trimethylsilyl, triethylsilyl, triisopropylsilyl and t-butyldimethylsilyl groups, and diphenyl($C_1$–$C_4$)alkylsilyl groups such as diphenylmethylsilyl and t-butyldiphenylsilyl groups, and phenyl di($C_1$–$C_4$)alkylsilyl groups such as phenyldimethylsilyl group and tribenzylsilyl group. Among these, the t-butyldimethylsilyl group is especially preferred.

Examples of the group which forms an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, and 6,6-dimethyl-3-oxa-2-oxobicyclo[3.1.0]hex-4-yl groups. Of these, the 2-tetrahydropyranyl, 2-tetrahydrofuranyl, 1-ethoxyethyl, 2-methoxy-2-propyl, (2-methoxyethoxy)methyl and 6,6-dimethyl-3-oxa-2-oxobicyclo[3.1.0]hex-4-yl groups are preferred.

Specific examples of the compound of formula (1) will be apparent from the definition of $R^2$ and its specific examples given above.

The enantiomorph of the compound of formula (1) is represented by the following formula (1)'

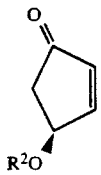

(1)' wherein $R^2$ is as defined above.

The 4-substituted-cyclopentenone used as the starting material in step (A) is a compound of formula (1) or (1)', or a mixture of the compounds (1) and (1)' in arbitrary ratios. An equimolar mixture of the compounds of formula (1) and (1)' is a racemic mixture, and a mixture of these in different proportions shows varying degrees of specific rotation according to their mixing ratios.

$R_B$ in formula (2) representing the organolithium compound represents a substituted or unsubstituted $C_2$-$C_{10}$ alkyl or alkenyl group.

The unsubstituted $C_2$-$C_{10}$ alkyl group may be linear or branched, and includes, for example, ethyl, propyl, butyl, isobutyl, sec-butyl, t-butyl, pentyl, hexyl, heptyl, octyl, nonyl and decyl groups.

The unsubstituted $C_2$-$C_{10}$ alkenyl group may be linear or branched, and includes, for example, vinyl, 1-propenyl, 1-butenyl, 1-pentenyl, 1-hexenyl, 1-heptenyl, 1-octenyl, 1-nonyl and 1-decyl group. They may be isomers of either E or Z type.

Examples of the substituent on the substituted $C_2$-$C_{10}$ alkyl group for $R_B$ are $C_3$-$C_7$ cycloalkyl groups, a vinyl group, $C_2$-$C_4$ alkynyl groups, a phenyl group and a phenoxy group (the phenyl and phenoxy groups may further be substituted by fluoro, methyl, trifluoromethyl or trifluoromethoxy), $C_1$-$C_4$ alkoxy groups and groups of the formula $OR^2$ where $R^2$ is as defined hereinabove.

Examples of the substituent on the substituted $C_2$-$C_{10}$ alkenyl group for $R_B$ include $C_1$-$C_4$ alkyl groups, $C_3$-$C_7$ cycloalkyl groups, $C_2$-$C_4$ alkynyl groups, a phenyl group and a phenoxy groups (the phenyl and phenoxy groups may further be substituted by fluoro, methyl, trifluoromethyl or trifluoromethoxy), $C_1$-$C_4$ alkoxy groups and groups of the formula $OR^2$ where $R^2$ is as defined above.

Specific examples of the substituents include alkyl groups having 1 to 4 carbon atoms such as methyl ethyl, propyl and butyl groups; cycloalkyl groups having 3 to 7 carbon atoms such as cyclopentyl and cyclohexyl groups; a vinyl group; alkynyl groups having 2 to 4 carbon atoms such as ethynyl, propargyl, 1-butynyl and 1-propynyl groups; phenyl, fluorophenyl, tolyl, trifluoromethylphenyl, trifluoromethoxyphenyl, phenoxy, fluorophenoxy, methylphenoxy, trifluoromethyl-phenoxy and trifluoromethoxyphenoxy groups; and alkoxy groups having 1 to 4 carbon atoms such as methoxy, ethoxy, propoxy and butoxy. Specific examples of $OR^2$ as the substituent will be apparent from the examples given above for formula (1).

Specific examples of the organolithium compound (2) having such a substituted or unsubstituted alkyl or alkenyl group having 2 to 10 carbon atoms will be apparent from the specific examples of $R_B$ given above. Compounds represented by the following formula

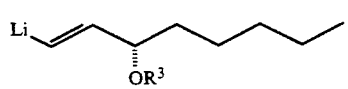

(2)-A wherein $R^3$ represents a tri($C_1$-$C_7$)hydrocarbon silyl group or $OR^3$ represents an acetal linkage, are especially preferred.

The sole reason for the preference of the organolithium compounds of formula (2)-A is that they partly agree with the skeleton of natural prostaglandin.

Q in formula (3) representing the copper compound represents a halogen atom such as chlorine, bromine or iodine atom, a cyano group, a phenylthio group or a 1-pentenyl group.

Examples of the copper compound will be apparent from the definitions of Q above.

In the conjugate addition reaction step (A) of the present invention, the organocopper compound formed from the organolithium compound (2) and the copper compound (3) is used.

The organocopper compound from the orgaolithium compound (2) and the copper compound (3) can be obtained by the methods described, for example, in G. H. Posner, Organic Reaction, vol. 19, 1 (1972); and Noyori et al., Tetrahedron Letters, 21, 1247 (1980), 23, 4057 (1982), 23, 5563 (1982), 24, 1187 (1983), 24, 4103 (1983), 25, 1383 (1984), and Isr. J. Chem., 24, 118 (1984). The descriptions of these literature references may be cited as part of the disclosure of the present specification.

For example, the organocopper compound may be prepared by reacting the organolithium compound and a copper salt in an inert solvent, for example a hydrocarbon such as benzene, hexane or heptane or an ether such as diethyl ether or dimethoxyethane at room temperature to $-78°$ C. for not more than several hours, for example for 0.5 hour at $-78°$ C.

Preferably, the conjugate addition reaction in step (A) is caused to proceed smoothly by using a trivalent organophosphorus compound, for example a trialkylphosphine (such as triethylphosphine or tributylphosphine), a trialkyl phosphite (such as trimethyl phosphite, triethyl phosphite, triisopropyl phosphite or tri-n-butyl phosphite), hexamethylphosphoric triamide or triphenyl phosphine. Tributylphosphine, and hexamethylphosphoric triamide can be preferably used.

The step (A) of the process of this invention is carried out advantageously by reacting the 4-substituted-2-cyclopentenone represented by formula (1) with the organocopper compound in the presence of the trivalent organophosphorus compound and an aprotic inert organic medium.

The 4-substituted-2-cyclopentenone and the organocopper compound stoichiometrically react in equimolar proportions. Usually, 0.5 to 2.0 moles, preferably 0.8 to 1.5 moles, especially preferably 1.0 to 1.3 moles, of the organocopper compound is used per mole of the 4-substituted-2-cyclopentenone.

The reaction in step (A) is carried out at a temperature of, for example, −100° to 20° C., preferably −78° C. to 0° C. The reaction time varies depending upon the reaction temperature. Usually, the reaction proceeds sufficiently if it is carried out at −78° to −20° C. for about 1 hour.

Advantageously, the reaction is carried out in the presence of an organic medium. Suitable organic media are inert and aprotic and do not react with the reagents.

Examples of the aprotic inert organic media include saturated hydrocarbons such as pentane, hexane, heptane and cyclohexane; aromatic hydrocarbons such as benzene, toluene and xylene; ethers such as diethyl ether, tetrahydrofuran, dioxane, dimethoxyethane and diethylene glycol dimethyl ether, and aprotic polar solvents such as hexamethylphosphoric triamide (HMP), N,N-dimethylformamide (DMF), N,N-dimethylacetamide (DMAC), dimethyl sulfoxide, sulfolane and N-methylpyrrolidone. These media may be used as a mixture of two or more. The inert medium used to produce the organocopper compound may be directly used as the aprotic inert organic medium. In this case, the 4-substituted-2-cyclopentenone is added to the reaction system in which the organocopper compound has been produced, and then the reaction is carried out. The amount of the organic medium may be that which is sufficient to allow the reaction to proceed smoothly. Usually, it is 1 to 100 times, preferably 2 to 20 times, the weight of the 4-substituted-2-cyclopentenone.

The trivalent organic phosphorus compound may be caused to be present during the preparation of the organocopper compound, and the 4-substituted-2-cyclopentenone may be added to this reaction system and then reacted.

Consequently, in step (A) of the process of this invention, a "conjugate added enolate" in which the organic group moiety $R_B$ adds to the 3-position of the 4-substituted-2-cyclopentenone is formed.

In step (B) of the process of this invention, the resulting enolate is reacted with the halide of formula (5) in the presence of the organotin compound of formula (4).

In formula (4) representing the organotin compound, the three R's are identical or different and each represents an alkyl group having 1 to 4 carbon atoms, a cycloalkyl group having 3 to 7 carbon atoms, a phenyl group, or a halogen atom. The two or three R's are not simultaneously halogen atoms.

According to the definition of R, examples of the organotin compound include tri($C_1$–$C_4$)alkyltin chlorides such as trimethyltin chloride, trimethyltin bromide, triethyltin bromide, tripropyltin chloride, tributyltin chloride and tributyltin bromide; tri($C_1$–$C_4$)alkyltin bromides; dialkyltin dihalides such as diemthyltin dichloride, diethyltin dichloride and dibutyltin dichloride; tributyltin triflate; tri($C_3$–$C_7$)cycloalkyltin halides such as tricyclohexyltin chloride, tricyclohexyltin bromide, tricyclopentyltin bromide and tricyclopentyltin chloride; triphenyltin chloride; di($C_3$–$C_7$)cycloalkyltin dihalides such as dicyclohexyltin dichloride and dicyclopentyltin dichloride; diphenyltin dihalides such as diphenyltin dichloride and diphenyltin dibromide; and triphenyltin triflate and tricycloyhexyltin triflate.

Preferred compounds of formula (4) are those in which the three R's are identical or different and each represents a butyl, cyclohexyl or phenyl group, and tributyltin chloride, triphenyltin chloride, and tricyclohexyltin chloride are especially preferred, and triphenyl tin chloride is most preferred.

The halide used in step (B) is represented by formula (5).

$$X-CH_2-Z-R_A \qquad (5)$$

In formula (5), X represents a halogen atom or a tosyl group, Z represents an ethylene group, an ethynylene group, a trans-vinylene group, a cis-vinylene group, a phenylene group

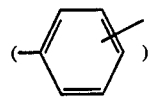

or a phenyleneoxa group

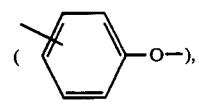

and $R_A$ represents a hydrogen atom or a substituted or unsubstituted $C_1$–$C_7$ alkyl or alkenyl group.

The substituted or unsubstituted $C_1$–$C_7$ alkyl or alkenyl group for $R_A$ in formula (5) may be linear or branched, and includes, for example, methyl, ethyl, propyl, isopropyl, butyl, isobutyl, sec-butyl, t-butyl, pentyl, hexyl and heptyl groups.

The unsubstituted $C_1$–$C_7$ alkenyl group for $R_A$ may be linear or branched, or a group bonded to the carbon atom of the group Z forming a direct double bond, such as =$CH_2$, or an alkenyl group bonded to the carbon atom of the group Z through a single bond.

Examples of the unsubstituted $C_1$–$C_7$ alkenyl group include vinyl, 1-propenyl, 1-butenyl, 1-pentenyl, 1-hexenyl, 1-heptenyl, 2-propenyl, 2-butenyl, 2-pentenyl, 2-hexenyl, 2-heptenyl, 3-butenyl, 3-pentenyl, 3-hexenyl, and 3-heptenyl groups. They may be of an E- or Z-type isomeric form.

Examples of the substituent on the substituted $C_1$–$C_7$ alkyl group include cycloalkyl groups having 3 to 7 carbon atoms, a vinyl group, alkynyl groups having 2 to 4 carbon atoms, a phenyl group and a phenoxy group (the phenyl and phenoxy groups may further be substituted by fluoro, methyl, trifluoromethyl or trifluoromethoxy), alkoxy groups having 1 to 4 carbon atoms, groups of the formula $OR^2$ in which $R^2$ is as defined above, acyloxy groups having 1 to 4 carbon atoms, an oxo group, and alkoxycarbonyl groups having 1 to 4 carbon atoms in the alkyl moiety.

Examples of the substituent on the substituted $C_1$–$C_7$ alkenyl group include alkyl groups having 1 to 4 carbon atoms, cycloalkyl groups having 3 to 7 carbon atoms, alkynyl groups having 2 to 4 carbon atoms, a phenyl group and a phenoxy group (the phenyl and phenoxy groups may further be substituted by fluoro, methylw trifluoromethyl or trifluoromethoxy), alkoxy groups having 1 to 4 carbon atoms, groups of the formula $OR^2$ in which $R^2$ is as defined above, acyloxy groups having 1 to 4 carbon atoms, an oxo group, and alkoxycarbonyl groups having 1 to 4 carbon atoms in the alkyl moiety.

Examples of the above substituents include alkyl groups having 1 to 4 carbon atoms such as methyl, ethyl, propyl and butyl groups; cycloalkyl groups having 3 to 7 carbon atoms such as cyclopentyl and cyclohexyl groups, a vinyl group; alkynyl groups having 2 to 4 carbon atoms such as ethynyl, propargyl, 1-butynyl and 1-propynyl groups; phenyl, fluorophenyl, tolyl, trifluoromethylphenyl, trifluoromethoxyphenyl, phenoxy, fluorophenoxy, methylphenoxy, trifluoromethylphenoxy and trifluormethoxyphenoxy groups; alkoxy groups having 1 to 4 carbon atoms such as methoxy, ethoxy, propoxy and butoxy groups; acyloxy groups having 1 to 4 carbon atoms such as acetoxy and propionyloxy groups, an oxo group; and lower alkoxycarbonyl groups such as methoxycarbonyl, ethoxycarbonyl and t-butoxycarbonyl groups. Specific examples of $OR^2$ as the substituent will be apparent from the examples given hereinabove with respect to formula (1).

Preferred examples of the halide of formula (5) are compounds represented by the following formula

   (5)—1 wherein X is as defined in formula (5), $R^1$ represents a $C_1$-$C_{10}$ alkyl group, a substituted or unsubstituted phenyl group, a substituted or unsubstituted $C_3$-$C_7$ cycloalkyl group, or substituted or unsubstituted phenyl ($C_1$-$C_2$)alkyl group, n is an integer of 1 to 9, and compounds represented by the following formula

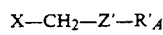   (5)—2 wherein X is as defined in the above formula, Z' represents an ethynylene, trans-vinylene, cisvinylene, phenylene or phenyleneoxa group, and $R'_A$ represents a $C_1$-$C_7$ alkenyl group whose position remotest from the group Z' is substituted by a substituent —$COOR^1$ in which $R^1$ is as defined above.

In formulae (5)-1 and (5)-2, X is a halogen atom, and $R^1$ is a $C_1$-$C_{10}$ alkyl group, a substituted or unsubstituted pheny group, a substituted or unsubstituted $C_3$-$C_7$ cycloalkyl group or a substituted or unsubstituted phenyl ($C_1$-$C_2$)alkyl group.

The $C_1$-$C_{10}$ alkyl group may be linear or branched, and includes, for example, methyl, ethyl, propyl, isopropyl, butyl, isobutyl, sec-butyl, t-butyl, pentyl, hexyl, heptyl, octyl, nonyl and decyl groups.

Examples of preferred substituents for the substituted or unsubstituted phenyl group include halogen atoms, a protected hydroxyl group, acyloxy groups having 2 to 7 carbon atoms, $C_1$-$C_4$ alkyl groups optionally substituted by halogen atoms, $C_1$-$C_4$ alkoxy groups optionally substituted by halogen atoms, a nitrile group and ($C_1$-$C_6$) alkoxycarbonyl groups. The halogen atoms are, for example, fluorine, chlorine and bromine, the first two being particularly preferred. Examples of the $C_2$-$C_7$ acyloxy groups are acetoxy, propionyloxy, butyryloxy, isobutyryloxy, valeryloxy, isovaleryloxy, caproyloxy, enanthyloxy and benzoyloxy groups.

Examples of the $C_1$-$C_4$ alkyl groups optionally substituted by halogen atoms preferably include methyl, ethyl, isopropyl, butyl, chloromethyl, dichloromethyl and trifluoromethyl groups. Examples of the $C_1$-$C_4$ alkoxy groups optionally substituted preferably include methoxy, ethoxy, propoxy, butoxy, chloromethoxy, dichloromethoxy and trifluoromethoxy groups. Examples of the ($C_1$-$C_6$)alkoxycarbonyl groups are methoxycarbonyl, ethoxycarbonyl, t-butoxycarbonyl and hexyloxycarbonyl groups.

The substituted phenyl group may have 1 to 3 substituents exemplified above, preferably one such substituent.

The substituted or unsubstituted $C_3$-$C_7$ cycloalkyl groups are, for example, unsubstituted saturated or unsaturated $C_3$-$C_7$, preferably $C_5$-$C_6$, especially preferably $C_6$, cycloalkyl groups optionally substituted by the aforesaid substituents, and examples include cyclopropyl, cyclopentyl, cyclohexyl, cyclohexenyl and cycloheptyl groups.

Examples of the substituted or unsubstituted phenyl ($C_1$-$C_2$)alkyl groups are benzyl, alpha-phenethyl and beta-phenethyl groups in which the phenyl group is unsubstituted or substituted by the aforesaid substituents.

In formula (5)-1, n is an integer of 1 to 9.

In formula (5)-2, Z' is an ethynylene group (—C≡C—), a trans-vinylene group

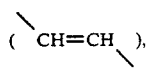

a cis-vinylene group

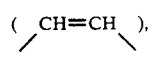

a phenylene group

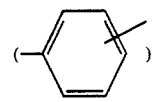

or a phenyleneoxa group

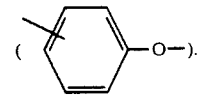

In formula (5)-2, $R'_A$ is a $C_1$-$C_7$ alkenyl group whose position remotest from the group Z' is substituted by a substituent —$COOR^1$ wherein $R^1$ is as defined hereinabove.

When the $C_1$-$C_7$ alkenyl group is, for example, 1-propenyl (—C≡C—$CH_2$) and Z' is an ethynylene group, —Z'—$R'_A$ is —CH=CH—CH=CH—$CH_2$—$COOR^1$.

In step (B) of the process of this invention, the conjugate added enolate formed in step (A) and being present in the reaction system is reacted with the halide of formula (5), (5)-1 or (5)-2. The reaction is carried out by first adding the organotin compound to the reaction system in which the organocopper compound has been introduced into the 4-substituted-2-cyclopentenone by conjugate addition reaction, and thereafter adding the halide of formula (5) which may be diluted with the aforesaid aprotic organic medium.

It is believed that stoichiometrically, the organotin compound and the enolate react in equimolar proportions to form a tin enolate freshly. Usually, the organotin compound is used in an amount of 0.8 to 1.5 moles, especially 1.0 to 1.2 moles, per mole of the 4-substituted-2-cyclopentenone initially used.

The reaction temperature is −100° to 0° C., preferably −78° to −20° C. It is sufficient that the reaction time is usually within 1 hour.

Stoichiometrically, the halide of formula (5) reacts with the enolate formed by conjugate addition-reaction in equimolar proportions. Usually, the halide is used in an amount of 0.8 to 5.0 moles, particularly 1.0 to 2.0 moles, per mole of the 4-substituted-2-cyclopentenone initially used.

The reaction temperature is −100° to 0° C., preferably −78° to −20° C. The reaction time varies depending upon the type of the halide used and the reaction temperature. Usually the reaction is terminated by carrying it out for about 1 hour to 50 hours at a temperature of −78° to −30° C. The end point of the reaction may be efficiently determined by monitoring it by, for example, thin-layer chromatography.

Preferably, the alkylation reaction in step (B) with the halide of formula (5) in the process of this invention is carried out in the aforesaid aprotic polar solvent, especially in the presence of hexamethylphosphoric triamide, and this frequently gives good results. After the reaction, the final desired product is isolated and purified by ordinary means such as post-treatment, extraction, washing, chromatography, distillation, or combinations of these.

Thus, according to this invention, there can be produced a 2,3-disubstituted-4-substituted cyclopentanone represented by the following formula

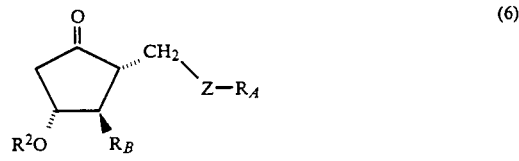

(6)

wherein $R_A$, $R_B$, $R^2$ and $Z$ are as defined above, an enantiomorph thereof represented by the following formula

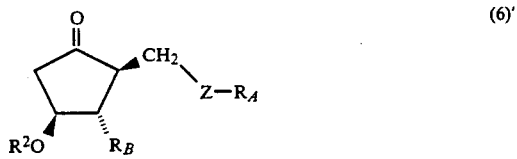

(6)' wherein $R_A$, $R_B$, $R^2$ and $Z$ are as defined above, or a mixture of the compounds of formulae (6) and (6)' in arbitrary ratios.

Among the compounds represented by formula (6), those represented by the following formula

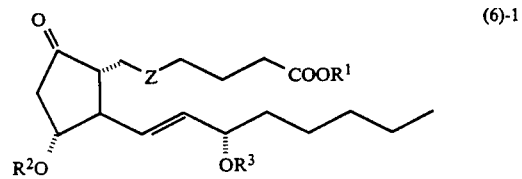

(6)-1 wherein $R^1$, $R^2$, $R^3$ and $Z$ are as defined above, are preferred.

Compounds of formula (6)-1 wherein $Z$ is a cisvinylene group have a $PGE_2$ skeleton; those in which $Z$ is an ethynylene group have a 5,6-dehydro $PGE_2$ skeleton; and those in which $Z$ is an ethylene group have a $PGE_1$ skeleton. The present invention should be fully evaluated as a process which can give such useful compounds.

To demonstrate the utility of the compounds produced by the process of this invention, the following flow chart is given which shows the conversion of a 5,6-dehydro $PGE_2$ derivative as a starting material into $PGE_2$, $E_1$, $F_{2\alpha}$, $F_{1\alpha}$, $D_2$, $D_1$ and $I_2$ respectively.

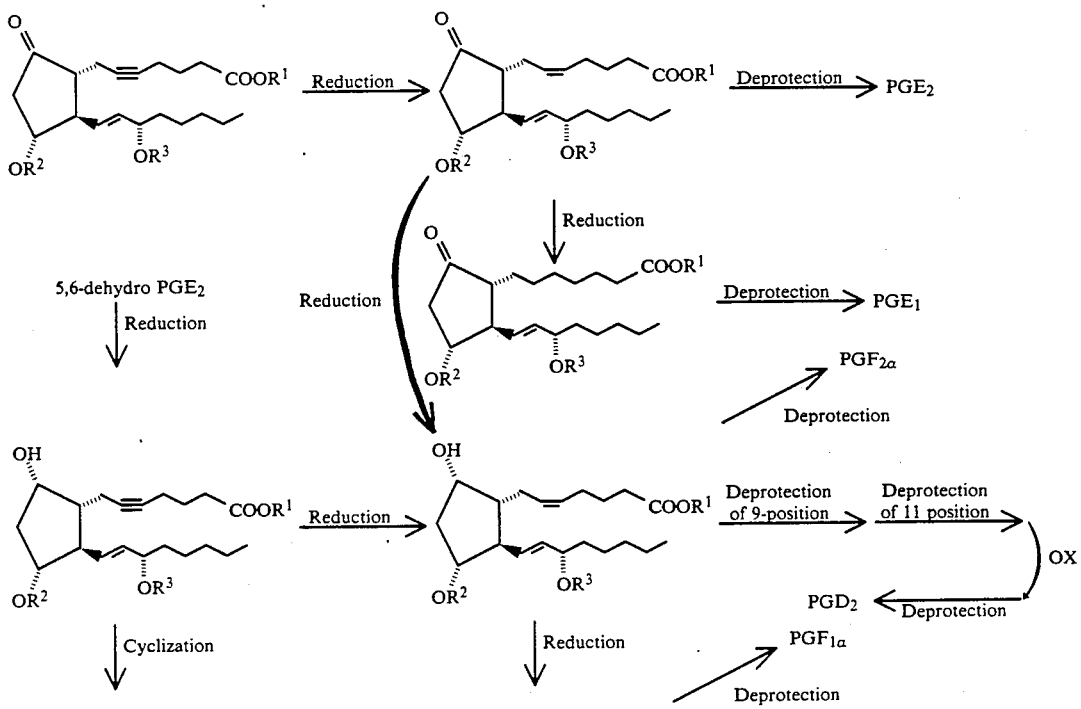

-continued

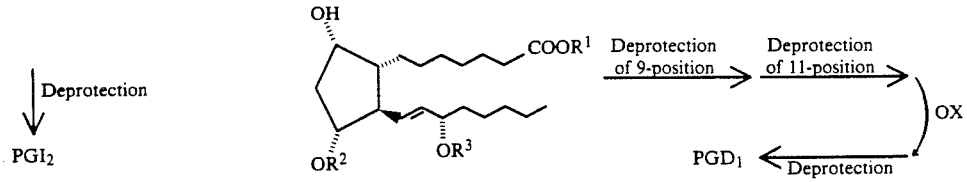

The following Referential Examples 1 to 5 specifically show some of the above conversion reactions. The other conversions reactions have already been reported by some of the present inventors.

One characteristic of the process of this invention is that all the reactions used proceed stereospecifically. Hence, a compound having the steric configuration represented by formula (6) is obtained from a starting material having the steric configuration represented by formula (1), and the enantiomorph of formula (6)' is obtained from the enantiomorph of formula (1)'. Accordingly, from a mixture of these compounds in an arbitrary ratio, a mixture reflecting the mixing ratio is obtained as a final product. Furthermore, since the organolithium compound of formula (2)-A contains an asymmetric carbon, it includes two optical isomers, but any of these optically active isomers or a mixture of them in an arbitrary ratio can be used. Among these, compounds having the steric configuration represented by formula (6)-1 are especially useful stereoisomers because they have the same steric configuration as natural prostaglandins.

The following examples illustrate the present invention more specifically. It should be understood however that the invention is not limited to these specific examples.

EXAMPLE 1

Synthesis of (2R,3R,4R)-3-butyl-4-t-butyldimethylsilyloxy-2-(2-octynyl)cyclopentanone

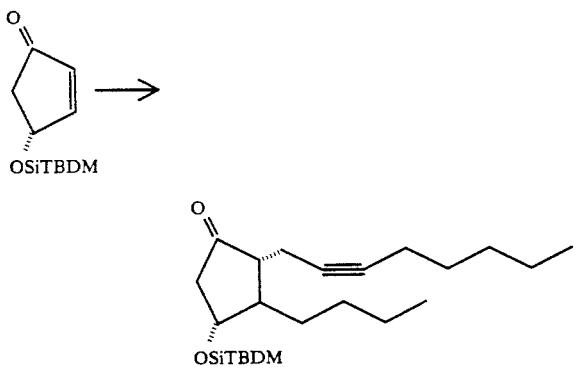

TBDM is an abbreviation for t-butyldimethyl.

(i) Cuprous iodide (99.1 mg; 0.52 mmole) was weighed into a 30 ml reaction tube purged with argon, and the inside of the tube was dried under reduced pressure. Then, the reaction tube was again purged with argon. Dry tetrahydrofuran (2 ml) and tributylphosphine (0.337 ml; 1.35 mmole) were introduced into the reaction tube, and stirred at 20° C. with stirring to form a uniform solution. The solution was cooled to −78° C., and n-butyllithium (1.60M, 0.325 ml, 0.52 mmole) was added, and the mixture was stirred at −78° C. for 10 minutes. Then, a solution of (R)-4-t-butyldimethylsiloxy-2-cyclopentenone (100 mg, 0.471 mmole) in tetrahydrofuran (2 ml) was added dropwise at −78° C. over 10 minutes. The mixture was stirred at −78° C. for 10 minutes. Then, hexamethylphosphoric triamide (1 ml) was added, and the mixture was stirred for 40 minutes at −78° C. Tributyltin chloride (0.14 ml, 0.520 mmole) was added, and the temperature was raised to −40° C. A solution of 1-iodo-2-octyne (184 mg, 0.78 mmole) in tetrahydrofuran (1 ml) was added, and the mixture was stirred for 2 hours. Ether (5 ml) was added to the reaction mixture, and the mixture was successively washed with a saturated aqueous solution of ammonium chloride (5 ml), a saturated aqueous potassium thiocyanate solution (5 ml) and a saturated aqueous sodium chloride solution (5 ml). The separated organic layer was dried over anhydrous sodium sulfate. The dried product was filtered and concentrated under reduced pressure. The resulting crude product was separated by silica gel column chromatography (Merck 7734, 6% water, 20 g; hexane:ethyl acetate=30:1) to give (2R,3R,4R)-3-butyl-4-t-butyldimethylsiloxy-2-(2-octynyl)cyclopentanone (88.1 mg, 0.233 mmole, 49%).

TLC: Rf=0.39 (hexane:ethyl acetate=10:1.

IR (liquid film): 1750, 1450, 1247, 1098, 834 and 771 cm$^{-1}$.

NMR (CDCl$_3$)δ: 0.05 and 0.09 (each s, 6, SiCH$_3$×2), 0.89 (s, 15, SiC(CH$_3$)$_3$, CH$_3$×2), 1.1–1.7 (m, 12, CH$_2$×6), 1.8–2.4 (m, 5, CH$_2$C≡C×2, CH×1), 2.4–2.8 (m, 3, CH$_2$CO×2, CHCO), 4.05 (dd, 1, J=13.0 and 6.4 Hz, CHOSi).

$^{13}$C NMR (CDCl$_3$)δ: −4.9, −4.5, 13.9 (for 2), 18.6, 19.1, 22.1, 22.9, 25.7 (for 4), 28.7, 29.0, 31.0, 31.7, 47.7, 48.6, 52.5, 73.3, 77.0, 81.9, 215.4.

MS (74 eV; m/e): H 378 (M$^+$), 321 (M$^+$—C$_4$H$_9$).

(ii) Cuprous iodide (198 mg; 1.04 mmole) was weighed into a 150 ml reaction tube purged with argon, and the inside of the tube was dried under reduced pressure. Then, the reaction tube was again purged with argon. Dry tetrahydrofuran (10 ml) and tributylphosphine (0.673 ml; 2.70 mmoles) were introduced into the reaction tube, and stirred at 19° C. with stirring to form a uniform solution. The solution was cooled to −78° C., and n-butyllithium (1.60M, 0.647 ml, 1.04 mmoles) was added, and the mixture was stirred at −78° C. for 10 minutes. Then, a solution of (R)-4-t-butyldimethylsiloxy-2-cyclopentenone (200 mg, 0.942 mmole) in tetrahydrofuran (15 ml) was added dropwise at −78° C. over 0.8 hours using a syringe drive. The mixture was stirred at −78° C. for 10 minutes. Then, hexamethylphosphoric triamide (2 ml) was added, and the mixture was stirred for 40 minutes at −78° C. Tributyltin chloride (0.28 ml, 1.04 mmole) was added, and the temperature was raised to −30° C. A solution of 1-bromo-2-octyne (197 mg, 1.04 mmole) in tetrahydrofuran (2 ml) was added, and the mixture was stirred for 17.5 hours. Ether (10 ml) was added to the reaction mixture, and the mixture was successively washed with a saturated aqueous ammonium chloride solution (10 ml), a saturated aqueous potassium thiocyanate solution (10 ml) and a saturated aqueous sodium chloride solution (10 ml). The separated organic layer was dried over anhydrous sodium sulfate. The dried product was filtered and concentrated under reduced pressure. The resulting crude product was separated by silica gel column chromatography (Merck 7734, 6% water, 20 g; hexane:ethyl acetate=30:1) to give (2R,3R,4R)-3-butyl-4-t-butyldimethylsiloxy-2-(2-octynyl)cyclopentanone (58.8 mg, 0.155 mmole, 16%) which coincided with the product obtained in (i) above.

EXAMPLE 2

Synthesis of 11,15-bis(t-butyldimethylsilyl)5,6-dehydroprostaglandin E$_2$ methyl ester:

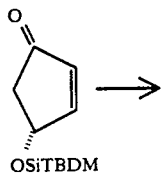

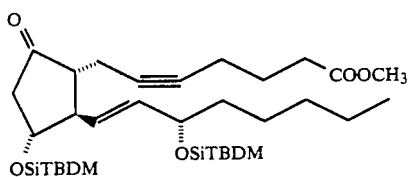

(i) A solution of (E,3S)-3-t-butyldimethylsiloxy-1-iodo-1-octene (354 mg, 0.961 mmole) in dry ether (5 ml) was put in a 150 ml reaction tube purged with argon, and cooled to −95° C. Then, t-butyllithium (1.77M, 1.09 ml, 1.92 mmoles) was added dropwise and the mixture was stirred for 3 hours at −95° to −78° C.

Separately, cuprous iodide (183 mg, 0.961 mmole) was weighed into a 30 ml eggplant-shaped flask. The inside of the tube was dried under reduced pressure and again purged with argon. Tetrahydrofuran (4 ml) and tributylphosphine (0.62 ml, 2.50 mmoles) were added, and the mixture was stirred at 21° C. to form a uniform solution. The uniform solution was added at a time to the above prepared alkenyl lithium solution under argon pressure using a stainless steel tube. The mixture was stirred at −78° C. for 5 minutes. Then, a solution of (R)-4-t-butyldimethylsiloxy-2-cyclopentenone (200 mg, 0.942 mmole) in tetrahydrofuran (15 ml) was added dropwise over 1 hour at −78° C. using a syringe drive. The mixture was stirred at −78° C. for 1 hour. Thereafter, hexamethylphosphoric triamide (2 ml) was added, and the mixture was stirred at −78° C. for 1 hour. Then, tributyltin chloride (0.26 ml, 0.961 mmole) was added, and the temperature was raised to −45° C. A solution of 1-iodo-6-methoxycarbonyl-2-hexyne (276 mg, 1.04 millimoles) in tetrahydrofuran (2 ml) was added, and the mixture was stirred for 1 hour. Ether (20 ml) was added to the reaction mixture, and the mixture was successively washed with a saturated aqueous solution of ammonium chloride (30 ml), a saturated aqueous solution of potassium thiocyanate (30 ml) and a saturated aqueous solution of sodium chloride (30 ml). The separated organic layer was dried over anhydrous sodium sulfate. The dried product was filtered and concentrated under reduced pressure. The resulting crude product was separated by silica gel column chromatography (Merck 7734, 6% water, 40 g; hexane:ethyl acetate=40:1) to give 11,15-bis(t-butyldimethylsilyl)-5,6-dehydroprostaglandin E$_2$ methyl ester (105.6 rag, 0.178 mmole, 19%).

TLC: Rf=0.50 (ethyl acetate:hexane=1:5).

IR (liquid film): 1746, 1246, 827 and 767 cm$^{-1}$.

$^1$H NMR (CDCl$_3$—CCl$_4$=1:1)δ: 0.04 and 0.06 (each s, 12, SiCH$_3$×2), 0.89 (s, 18, SiC(CH$_3$)$_3$×2), 0.92 (t, 1, J=6.5 Hz, CH$_3$), 1.1–1.5 (m, 8, CH$_2$×4), 1.7–2.9 (m, 12, CH$_2$CO×2, CH$_2$C≡C×2, CH×2 and CH$_2$), 3.65 (s, 3, OCH$_3$), 4.05 (m, 2, CHOSi×2), 5.4–5.7 (m, 2, vinyl).

$^{13}$C NMR (CDCl$_3$)δ: −4.7, −4.5, (for 2), −4.2, 13.6, 14.0, 16.9, 18.0, 18.2, 22.6, 24.2, 25.0, 25.8 (for 3), 25.9, (for 3), 31.9, 32.7, 38.6, 47.7, 51.4, 51.9, 52.9, 72.7, 73.1, 77.3, 80.8, 128.2, 136.8, 173.4, 213.4.

$[α]_D^{21}$:−13.9° (C 1.59, CH$_3$OH).

(ii) A solution of (E,3S)-3-t-butyldimethylsiloxy-1-iodo-1-octene (354 mg, 0.961 mmole) in dry ether (5 ml) was added to a 150 ml argon-purged reaction tube, and cooled to 95° C. Then, t-butyllithium (1.77M, 1.09 ml, 1.92 mmoles) was added dropwise, and the mixture was stirred for 3 hours at −95° to −78° C.

Separately, cuprous iodide (183 mg, 0.961 mmole) was weighed into a 30 ml eggplant-shaped flask. The inside of the tube was dried under reduced pressure and again purged with argon. Tetrahydrofuran (4 ml) and tributylphosphine (0.62 ml, 2.50 mmoles) were added and stirred to form a uniform solution.

The uniform solution was added at a time to the alkenyllithium solution prepared above under argon pressure using a stainless steel tube. The stainless steel tube was washed with tetrahydrofuran (2 ml), and the washing was also added dropwise. The mixture was stirred at −78° C. for 5 minutes. Then, a solution of (R)-4-t-butyldinmethylsiloxy-2-cyclopentenone (200 mg, 0.942 mmole) in tetrahydrofuran (10 ml) was added dropwise over 30 minutes at −78° C. using a syringe drive. The mixture was stirred at −78° C. for 10 minutes. Thereafter, tributyltin chloride (0.26 ml, 0.961 mmole) was added, and the mixture was stirred at −78° C. for 1 hour. A solution of 1-iodo-6-methoxycarbonyl-2-hexyne (276 mg, 1.04 mmoles) in tetrahydrofuran (2 ml) was added, and the mixture was stirred for 20 minutes. Hexamethylphosphoric triamide (0.9 ml) was added, and the mixture was stirred at −78° C. for 15 minutes. The temperature was then elevated to −45° C., and the mixture was stirred for 30 minutes. Hexamethylphosphoric triamide (0.9 ml) was added, and the mixture was stirred for 1.5 hours. A saturated aqueous ammonium chloride solution (30 ml) was added to the reaction mixture, and the mixture was vigorously shaken. The mixture was separated into an organic layer and an aqueous layer. The organic layer was successively washed with a saturated aqueous solution of potassium thiocyanate (30 ml), and a saturated aqueous sodium chloride solution (30 ml), and then dried over anhydrous sodium sulfate. The dried product was filtered and concentrated under reduced pressure. The crude product obtained was separated by silica gel column chromatography (Merck 7734, 6% water, 40 g, ethyl acetate:hexane=1:40) to give 11,15-bis(t-butyldimethylsilyl)-5,6-dehydroprostaglandin E$_2$ methyl ester (173.9 mg, 0.293 mmole, 31%). The various spectral data of this product agreed with those given in section (i) above.

(iii) (E)-1-iodo-3-t-butyldimethylsiloxy-1-octene (593.1 mg, 1.61×10$^{-3}$ mole) and dry ether (6 ml) were taken into a 150 ml argon-purged reaction tube. Then, t-butyllithium (1.72 ml, 3.22×10⁻³ mole) was added by using a syringe, and the mixture was stirred at −95° to −78° C. for 3 hours. Separately, cuprous iodide (306.6 mg, 1.61×10⁻¹ mole) was taken into a 30 ml eggplant-shaped flask. The inside of the tube was dried under heat and reduced pressure, and then purged with argon. Dry tetrahydrofuran (6 ml) and tributylphosphine (1.04 ml, 4.19×10⁻³ mole) were added, and the mixture was stirred at 23° C. to form a uniform solution. The solution was cooled to −78° C., and added at a time to the above prepared vinyl lithium solution under argon pressure by means of a stainless steel tube. The mixture was stirred at −78° C. for 10 minutes. A solution of 4-t-butyldimethylsiloxy-2-cyclopentenone (325.6 mg, 1.53×10⁻³ mole) in THF (12 ml) was added dropwise over 1 hour. The reaction tube was washed with 1 ml of THF, and the mixture was further stirred for 10 minutes. HMPA (1.5 ml) was added, and the mixture was stirred for 30 minutes. Thereafter, a solution of triphenyltin chloride (627.6 mg, 1.61×10⁻³ mole) in 2 ml of THF was added, and after the temperature was elevated to −30° C., a solution of 1-iodo-6-carbomethoxy-2-hexyne (814.2 mg, 3.06×10⁻³ mole) in HMPA was added, and the mixture was stirred at −30° C. for 4.5 hours. Subsequently, the mixture was left to stand at −27° C. for 13 hours, and a saturated aqueous ammonium chloride solution (20 ml) was added. The mixture was vigorously shaken to separate it into an organic layer and an aqueous layer. The aqueous layer was extracted with ether (20 ml×2). The ethereal layers were combined, washed with a saturated aqueous solution of sodium chloride, and dried over anhydrous sodium sulfate. The dried product was filtered and concentrated under reduced pressure. The resulting crude product was separated by silica gel column chromatography (Merck 7734, 50 g, ethyl acetate:-hexane=1:60, 600 ml→1:20=ethyl acetate:hexane, 200 ml) to give dl-11,15-bis(t-butyldimethylsilyl)-5,6-dehydroprostaglandin E₂ methyl ester (542.1 mg, yield 59.7%).

IR (liquid film): 1746, 1246, 827 and 767 cm⁻¹.

(iv) The procedure of Example 2(iii) was repeated except that a solution of tributyl tin chloride (524 mg, 1.61×10⁻³ mole) was used in place of the solution of triphenyl tin chloride. As a result 291 mg (yield 32%) of dl-11, 15-bis(t-butyldimethylsilyl)-5,6-didehydroprostaglandin E₂ methyl ester was obtained.

IR (liquid film): 1746, 1246, 827 and 767 cm⁻¹.

EXAMPLE 3

Synthesis of 11,15-bis(t-butyldimethylsilyl)prostaglandin E₂ methyl ester

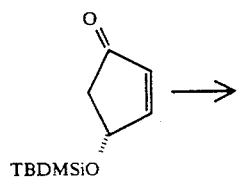

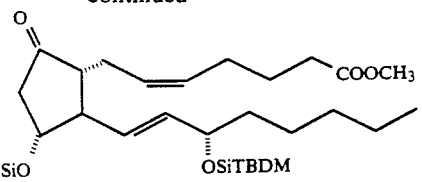

(i) A solution of (E, 3S)-3-t-butyldimethylsiloxy-1-iodo-1-octene (354 mg, 0.961 mmole) in dry ether (5 ml) was put in a 150 ml reaction tube purged with argon, and cooled to −95° C. Then, t-butyllithium (1.77M, 1.09 ml, 1.92 mmoles) was added dropwise, and the mixture was stirred for 3 hours at −95° to −78° C. Separately, cuprous iodide (183 mg, 0.961 mmole) was weighed into a 30 ml eggplant-shaped flask. The inside of the tube was dried under reduced pressure and purged again with rgon. Tetrahydrofuran (4 ml) and tributylphosphine (0.62 ml, 2.50 mmoles) were added, and the mixture was stirred at 29° C. to form a uniform solution. The uniform solution was added at once under argon pressure to the alkenyllithium solution prepared above by means of a stainless steel tube. The mixture was stirred at −78° C. for 5 minutes. Then, a solution of (R)-4-t-butyldimethylsiloxy-2-cyclopentenone (200 mg, 0.942 mmole) in tetrahydrofuran (10 ml) was added dropwise over 30 minutes by means of a syringe drive. The mixture was then stirred at −78° C. for 10 minutes. Thereafter, tributyltin chloride (0.26 ml, 0.961 mmole) was added, and the mixture was stirred at −78° C. for 30 minutes. Hexamethylphosphhoric triamide (1.8 ml) was added, and a solution of (Z)-1-iodo-6-methoxycarbonyl-2-hexene (279 mg, 1.04 mmoles) in tetrahydrofuran (2 ml) was added, and the temperature was raised to −45° C. The mixture was stirred for 2 hours. A saturated aqueous ammonium chloride solution (40 ml) was added to the reaction mixture, and the mixture was vigorously shaken to separate it into an organic layer and an aqueous layer. The organic layer was successively washed with a saturated aqueous potassium thiocyanate solution (40 ml) and a saturated aqueous sodium chloride solution (40 ml), and dried over anhydrous sodium sulfate. The dried product was filtered and concentrated under reduced pressure. The crude product was separated by silica gel column chromatography (Merck 7734, 40 g, ethyl acetate:hexane=1:20 to give 11,15-bis(t-butyldimethylsilyl)prostaglandin E₂ methyl ester (142.5 mg, 0.239 mmole, 25%).

TLC: Rf=0.58 (ethyl acetate:hexane=1:5).

IR (liquid film): 1743, 1243, 1000, 964, 927, 828 and 768 cm⁻¹.

¹H NMR (CDCl₃)δ: 0.03 and 0.06 (each s, 12, SiCH₃×2), 0.8-1.0 (m, 21, C—CH₃×7), 1.2-1.5 (m, 8, CH₂33 4), 1.6-2.9 (m, 12, CH₂CO×2, CH₂C=2, CH×2 and CH₂), 3.67 (s, 3, OCH₃), 4.06 (m, 2, CHO-Si×2), 5.37 (m, 2, vinyl), 5.54 (m, 2, vinyl).

[α]D²¹: −52.7° (C 1.28, CH₃OH).

(ii) (E)-1-iodo-3-t-butyldimethylsiloxy-1-octene (593.1 mg, 1.61×10⁻³ mole) and 6 ml of dry ether were taken into a 150 ml argon-purged reaction tube, cooled to −95° C., and kept stirred. t-Butyllithium (1.72 ml, 3.22×10⁻³ mole) was added by means of a syringe, and the mixture was stirred at −95° to −78° C. for 3 hours. Separately, cuprous iodide (306.6 mg, 1.61×10⁻³ mole) was taken into a 30 g eggplant-shaped flask. The inside of the tube was dried under heat and reduced pressure, and then purged with argon. Dry THF (6 ml) and tributylphosphine (1.04 ml, 4.19 ×10⁻³ mole) were added, and the mixture was stirred at 25° C. to form a uniform solution. The uniform solution was cooled to −78° C., and added at a time under argon pressure by means of a stainless steel tube to the vinyllithium solution prepared above. The mixture was stirred at −78° C. for 10 minutes. A solution of 4-t-butyldimethylsiloxy-2-cyclopentenone (325.6 mg, 1.53×10⁻³ mol) in THF (12 ml) was added dropwise over one hour. The reaction tube was washed with 1 ml of THF, and the mixture was further stirred for 10 minutes. HMPA (1.5 ml) was added, and the mixture was stirred for 30 minutes. Triphenyltin chloride (627.6 ml, 1.61×10⁻³ mole) in THF (2 ml) was added. The temperature was elevated to −30° C., and a solution of (Z)-1-iodo-6-carbomethoxy-2-hexene (1.231 g, 4.59×10⁻³ mole) in HMPA was added. The mixture was stirred at −30° C. for 3 hours. Subsequently, the reaction mixture was left to stand at −27° C. for 97.9 hours, and then a saturated aqueous ammonium chloride solution (20 ml) was added. The mixture was shaken vigorously to separate it into an organic layer and an aqueous layer. The organic layer was washed with a saturated aqueous sodium chloride solution and dried over anhydrous sodium sulfate. The dried product was filtered and concentrated under reduced pressure. The crude product was subjected to short chromatography (Merck 7734, 5 g, ethyl acetate:hexane=1:5) to remove highly polar substances (tributylphosphine and triphenyltin chloride). The product was purified by silica gel column chromatography (Merck 7734, 50 g, 1:60=ethyl acetate:hexane, 780 ml→1:20=ethyl acetate:hexane, 600 ml) to give dl-11,15-bis(t-butyldimethylsilyl)prostaglandin E₂ methyl ester (647 mg, yield 71%).

IR (liquid film): 1743, 1243, 1000, 964, 927, 828, and 768 cm⁻¹.

(iii) The procedure of Example 3(ii) was repeated except that 524 ml (1.61×10⁻³ mole) of tributyl tin chloride was used in place of triphenyl tin chloride. 173 mg (yield 19%) of dl-11, 15-bis(t-butyldimethylsilyl) prostaglandin E₂ methyl ester was obtained.

IR (liquid film): 1743, 1243, 1000, 964, 927, 828 and 768 cm⁻¹.

EXAMPLE 4

Synthesis of 11,15-bis(t-butyldimethylsilyl)prostaglandin E₁ methyl ester

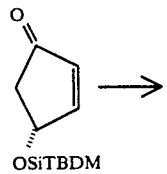

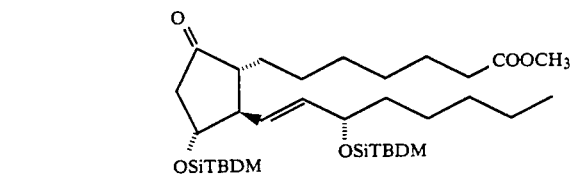

(E, 3S)-3-t-butyldimethylsiloxy-1-iodo-octene (607.8 mg; 1.65×10⁻³ mole) and 6 ml of dry ether were weighed into a 150 ml. argon-purged reaction tube, cooled to −95° C., and stirred. t-Butyllithium (1.92M, 1.72 ml, 3.30×10⁻³ mole) was added to the mixture by means of a syringe, and the mixture was stirred at −95° to −78° C. for 3 hours.

Separately, a 30 ml eggplant-shaped flask was provided, and cuprous iodide (314.2 mg; 1.65×10⁻³ mole) was weighed into it. The reaction mixture in the flask was dried by heating under reduced pressure, and then the reaction system was purged with argon. Dry THF (6 ml) and tributylphosphine (1.07 ml; 4.29×10⁻⁶ mole) were added, and the mixture was stirred at room temperature to form a uniform solution. The solution was cooled to −78° C. and added at a time to the above prepared vinyllithium solution by means of a stainless steel tube under argon pressure. After stirring at −78° C. for 10 minutes, a THF solution (12 ml) of (R)-4-t-butyldimethylsiloxy-2-cyclopentenone (318.5 mg, 1.50×10⁻³ mole) was added dropwise over 1 hour. The flask was further washed with 1 ml of THF, and the washing was added. The reaction mixture was stirred for 10 minutes. To the reaction mixture was added 1.5 ml of hexamethylphosphoric triamide (HMPA), and the mixture was stirred for 30 minutes. Then, a THF solution (2 ml) of triphenyltin chloride (643.2 mg; 1.65×10⁻³ mole) was added. The reaction solution was heated to −20° C., and an HMPA solution (2.87 ml) of methyl 6-iodohexanoate (2.0882 mg; 7.73×10⁻³ mole) was added. The mixture was stirred at −20° C. for 16 hours. After the reaction, 20 ml of a saturated aqueous solution of ammonium chloride was added, and the mixture was well shaken to separate it into an organic layer and an aqueous layer. The aqueous layer was extracted with ether (2×20 ml). The organic layers were combined and washed with a saturated aqueous sodium chloride solution (20 ml), and dried over anhydrous sodium sulfate. The desiccant was removed by filtration, and the residue was concentrated under reduced pressure. The concentrate was chromatographed on a silica gel column (Merck 7734, 5 g; 1:5=ethyl acetate:hexane). The resulting crude concentrated product was chromatographed on a column of silica gel (Merck 7734, 50 g; ethyl acetate:hexane=1:60, 900 ml→ethyl acetate:hexane=1:20, 600 ml) to give 178.7 mg (20%) of 11,15-bis(t-butyldimethylsilyl)prostaglandin E₁ methyl ester.

TLC: Rf=0.52 (ethyl acetate:hexane=1:5).

¹H NMR (CDCl₃)δ: 5.6–5.4 (m, 2H), 4.2–3.8 (m, 2H), 3.66 (s, 3H), 2.64 (dd, 1H, J=7.2, 18.4 Hz), 2.4–1.8 (m, 4H), 1.7–1.0 (m), 1.0–0.8 (m, 21H), 0.1–0.0 (m).

IR (neat): 1750 cm⁻¹.

EXAMPLE 5

Synthesis of (2R,3R,4R)-2-allyl-4-t-butyldimethylsilyloxy-3-[(E,3S)-3-t-butyldimethylsilyloxy-1-octenyl]cyclopentanone

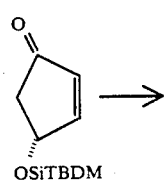

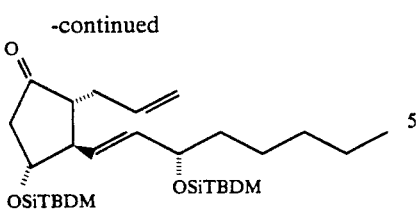

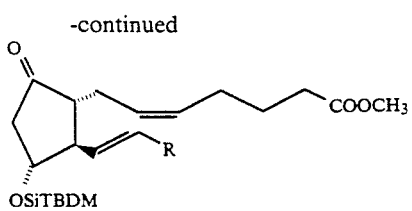

The procedure of Example 3 was repeated except that allyl iodide was used instead of (Z)-1-iodo-6-methoxycarbonyl-2-hexene. (2R,3R,4R)-2-allyl-4-t-butyldimethylsilyloxy-3-[(E,3S)-3-t-butyldimethylsilyloxy-1-octenyl]cyclopentanone was obtained in a yield of 71%.

$^1$H NMR (CDCl$_3$)δ: 0.07 (12H, s), 0.86 (21H, s), 1.1–1.5 (8H, m), 1.6–2.8 (6H, m), 3.8–4.3 (2H, m), 4.75–5.60 (5H, m).

IR (liquid film): 3100, 1745, 1255, 1110, 965, 910, 875, 835, 810 and 770 cm$^{-1}$.

MS (m/e): 494, 479, 437 and 379.

EXAMPLE 6

Synthesis of (2R,3R,4R)-4-t-butyldimethylsilyloxy-3-[(E,3E)-3-t-butyldimethylsilyloxy-1-octenyl]-2-(2-propynyl)cyclopentanone

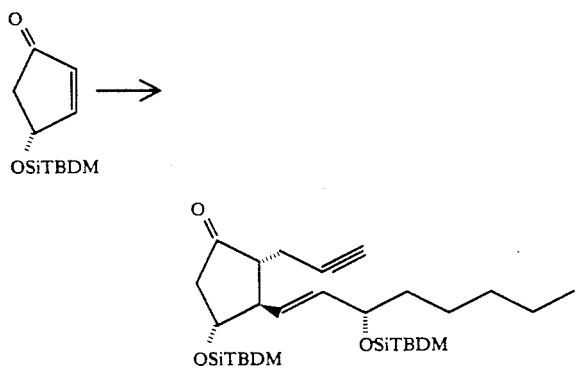

The procedure of Example 2 was repeated except that propargyl iodide was used instead of 1-iodo-6-methoxycarbonyl-2-hexyne. (2R,3R,4R)-4-t-butyldimethylsilyloxy-3-[(E,3S)-3-t-butyldimethylsilyloxy-1-octenyl]-2-(2-propargyl)cyclopentanone was obtained in a yield of 65%.

$^1$H NMR (CDCl$_3$)δ: 0.06 (12H, s), 0.87 (21H), 1.0–1.7 (8H, m), 1.8–3.0 (7H, m), 3.7–4.2 (2H, m), 5.3–5.6 (2H, m).

IR (liquid film): 3330, 1755, 1255, 1155, 1120, 1090, 1005, 965, 880, 835 and 775 cm$^{-1}$.

EXAMPLES 7–16

Syntheses of 11,15-bis(t-butyldimethylsilyloxy)prostaglandin E$_2$ methyl esters

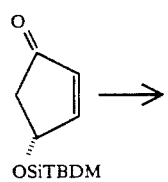

The following compounds were synthesized by the same procedure as in Example 3 using either tributyl tin chloride (i) or triphenyl tin chloride (ii). The results, together with the results of Examples 1, 2 and 3 are shown in the following Table 2.

Example 7: 11,15-bis(t-butyldimethylsilyl)-17(R),20-dimethylprostaglandin E$_2$ methyl ester Example 8: 11,15-bis(t-butyldimethylsilyl)-17(S),20-dimethylprostaglandin E$_2$ methyl ester Example 9: 11,15-bis(t-butyldimethylsilyl)-16,17,18,19,20-pentanor-15-cyclopentylprostaglandin E$_2$ methyl ester Example 10: 11,15-bis(t-butyldimethylsilyl)-16,17,18,19,20-pentanor-15-cyclohexylprostaglandin E$_2$ methyl ester Example 11: 11,15-bis(t-butyldimethylsilyl)-15-methylprostaglandin E$_2$ methyl ester Example 12: 11,15-bis(t-butyldimethylsilyl)-16,16-dimethylprostaglandin E$_2$ methyl ester Example 13: 11,15-bis(t-butyldimethylsilyl)-20-isopropylidene-17-methylprostaglandin E$_2$ methyl ester Example 14: 11,15-bis(t-butyldimethylsilyl)-18,18,19,19-tetradehydro-16-methylprostaglandin E$_2$ methyl ester Example 15: 11,15-bis(t-butyldimethylsilyl)-18,19,20-trinor-17-phenylprostaglandin E$_2$ methyl ester Example 16: 11-(t-butyldimethylsilyl)-15-deoxy-16-trimethylsilyloxy-16-vinylprostaglandin E$_2$ methyl ester The characteristic spectral data of the compounds obtained in Examples 7 to 16 are listed in Table 1.

EXAMPLES 17–18

Synthesis of 11,15-bis(t-butyldimethylsilyloxy)prostaglandin E$_2$ analogues

The following compounds were synthesized in the same way as in Example 1 and Examples 7–16 (yields 35–49%) using tributyl tin chloride as the organotin compound of formula (4).

Example 17: 11,15-bis(t-butyldimethylsilyl)-2,3-dehydro-17,18,19,20-tetranor-16-[3-(alpha,alpha,alphatrifluoromethyl)phenoxy]prostaglandin E$_2$ methyl ester Example 18: 11,15-bis(t-butyldimethylsilyl)-4,5,6-trinor-3,7-inter-m-phenylene-3-oxaprostaglandin E$_2$ methyl ester The characteristic spectral data of the compounds obtained in Examples 17 and 18 are shown in Table 1. The results (yield) for Example 17 is shown in the following Table 2.

EXAMPLES 19–20

Synthesis of prostaglandin E$_1$ methyl ester analogues

The following compounds were synthesized by the same procedure as in Example 4 (yields 17–32%).

Example 19: 11-(t-butyldimethylsilyl)-15-deoxy-14-methyl-16-trimethylsilyloxyprostaglandin E$_1$ methyl ester Example 20: (4Z)-Δ⁴-11-(t-butyl-dimethylsilyl)-15-deoxy-16-methyl-16-trimethylsilyloxyprostaglandin $E_1$ methyl ester The characteristic spectral data of the compounds obtained in Examples 19 and 20 are shown in Table 1.

TABLE 1

| Example | $^1$H NMR (CDCl$_3$) δ | IR (liquid film) cm$^{-1}$ | MS |
|---|---|---|---|
| 7 | 0.03 and 0.06 (12H, s), 0.8–1.0 (24H, m), 1.2–1.5 (9H, m), 1.6–2.9 (12H, m), 3.67 (3H, s), 3.9–4.2 (2H, m,) 5.25–5.5 (2H, m), 5.5–5.65 (2H, m). | 1745, 1245, 1000, 965, 930, 830, 770. | 565 (M − 57). |
| 8 | 0.03 and 0.06 (12H, s), 0.8–1.0 (24H, m), 1.2–1.5 (9H, m), 1.6–2.9 (12H, m), 3.67 (3H, s), 3.9–4.2 (2H, m,) 5.25–5.5 (2H, m), 5.5–5.65 (2H, m). | 1745, 1245, 1000, 965, 930, 830, 770. | 565 (M − 57). |
| 9 | 0.06 (12H), 0.8–1.0 (18H, s), 1.1–1.5 (9H, m), 1.6–2.9 (12H, m), 3.67 (3H, s), 3.9–4.2 (2H, m), 5.25–5.65 (4H, m). | 1745, 1245, 1000, 965, 930, 830, 770. | 535 (M − 57). |
| 10 | 0.06 (12H), 0.8–1.0 (18H, s), 1.1–1.5 (11H, m), 1.6–2.9 (12H, m), 3.67 (3H, s), 3.9–4.2 (2H, m), 5.25–5.65 (4H, m). | 1745, 1245, 1000, 965, 930, 830, 770. | 549 (M − 57). |
| 11 | 0.03 and 0.06 (12H, s), 0.90 (21H), 1.23 (3H, s), 0.9–1.6 (10H, m), 1.6–2.7 (10H, m), 3.65 (3H, s), 4.1 (1H, m), 5.5 (4H, m). | 1745, 1250, 1155, 1095, 1005, 835, 770. | 609 (M + 1). 551 (M − 57). |
| 12 | 0.06 (12H), 0.87 (21H), 1.14 (6H, s), 1.0–2.8 (18H, m), 3.60 (3H, s), 3.8–4.2 (2H, m), 5.2–5.6 (4H, m). | 1745, 1245, 1000, 965, 930, 830, 770. | 565 (M − 57). |
| 13 | 0.06 (12H), 0.87 (21H), 1.5–1.8 (6H, d), 1.0–2.8 (19H, m), 3.63 (3H, s), 3.8–4.2 (2H, m), 4.8–5.6 (4H, m), 6.5–7.2 (1H, m). | 1745, 1255, 1000, 965, 935, 835, 770. | 591 (M − 57). |
| 14 | 0.06 (12H), 0.87 (24H, m), 1.0–2.9 (19H, m), 3.65 (3H, s), 3.9–4.2 (2H, m), 5.25–5.6 (4H, m). | 2250, 1745, 1255, 1000, 970, 935, 830, 770. | 547 (M − 57). |
| 15 | 0.06 (12H), 0.87 (18H, s), 1.0–2.9 (16H, m), 3.63 (3H, s), 3.9–4.2 (2H, m), 5.3–5.6 (4H, m), 7.3 (5H, s). | 3030, 1745, 1600, 1255, 1005, 965, 935, 830, 770. | 571 (M − 57). |
| 16 | 0.05 (6H, s), 0.90 (9H, s), 0.87 (12H, s+t), 1.1–1.9 (16H, m), 2.1–2.6 (8H, m), 3.65 (3H, s), 4.2–4.5 (1H, m), 4.7–5.6 (7H, m). | 3080, 1745, 1250, 1005, 965, 930, 830, 770. | 563 (M − 57). |
| 17 | 0.06 (12H), 0.87 (21H, s+t), 1.0–2.9 (12H, m), 2.6 (2H, d), 3.73 (3H, s), 4.2–4.5 (2H, m), 4.67 (2H, s), 6.7–7.4 (4H, m). | 3050, 1745, 1600, 1585, 1255, 1090, 1055, 965, 835, 775. | 632 (M+). 575 (M − 57). |
| 18 | 0.06 (12H), 0.85 (18H, s), 1.1–3.0 (10H, m), 3.63 (3H, s), 3.93 (2H, d), 3.9–4.3 (2H, m), 5.2–5.7 (4H, m), 6.7–7.6 (6H, m). | 3050, 1745, 1725, 1600, 1315, 1255, 1005, 965, 930, 835, 770. | 696 (M+). 639 (M − 57). |
| 19 | 0.05 (6H, s), 0.10 (9H, s), 0.86 (12H, s+t), 1.15 (3H, s), 1.1–1.9 (16H, m), 2.1–2.6 (8H, m), 3.64 (3H, s), 4.2–4.5 (1H, m), 5.2–5.8 (2H, m). | 1740, 1250, 1170, 1100, 1060, 970, 860, 835, 775, 750. | 512. 395. 173. 58. |
| 20 | 0.05 (6H, s), 0.09 (9H, s), 0.85 (12H, s+t), 1.15 (3H, s), 1.0–2.7 (22H, m), 3.63 (3H, s), 4.2–4.5 (1H, m), 5.1–5.8 (4H, m). | 1740, 1255, 1170, 1100, 1060, 970, 860, 835, 770, 750. | 509 (M − 57). |

TABLE 2

| Example | R of R$_3$SnCl | Z | Yield (%) (Ph) | (Bu) |
|---|---|---|---|---|
| Ex. 1 (i) | Bu[1] | ≡ | | 49 |
| (ii) | Bu | ≡ | | 16 |
| Ex. 2 (i) | Bu | ≡ | | 19 |
| (ii) | Bu | ≡ | | 31 |
| (iii) | Ph[2] | ≡ | 59 | |
| (iv) | Bu | ≡ | | 32 |
| Ex. 3 (i) | Bu | = | | 25 |
| (ii) | Ph | = | 71 | |
| (iii) | Bu | = | | 19 |
| Ex. 7 | Ph | = | 65 | |
| 8 | Ph | = | 67 | |
| 9 | Ph | = | 61 | |
| 10 | Ph | = | 58 | |
| 11 | Bu | = | | 29 |
| 12 | Ph | = | 54 | |
| 13 | Bu | = | | 26 |
| 14 | Ph | = | 57 | |
| 15 | Bu | = | | 23 |
| 16 | Bu | = | | 19 |
| Ex. 17 | Bu | = | | 35 |

[1] Bu = Butyl
[2] Ph = Phenyl

REFERENTIAL EXAMPLE 1

Synthesis of 11,15-bis(t-butyldimethylsilyl)prostaglandin $E_2$ methyl ester

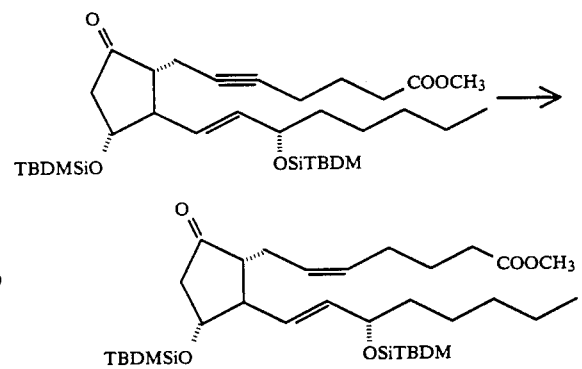

11,15-bis(t-butyldimethylsilyl)-5,6-dehydroprostaglandin $E_2$ methyl ester (48.2 mg; 0.081 mmole) and synthetic quinoline (25 mg) were dissolved in benzene (2.5 ml), and cyclohexane (2.5 ml) and then 5% Pd-BASO$_4$ (25 mg) were added. The mixture was stirred at 25° C. for 3 hours in an atmosphere of hydrogen. Then, synthetic quinoline (50 mg) and 5% PdBaSO$_4$ (50 mg) were additionally supplied, and the mixture was stirred at 40° C. for 4.5 hours. The catalyst was removed by filtration, and the filtrate was washed with ethyl acetate. The washings were combined, and concentrated under reduced pressure.

The concentrate was chromatographed on a silica gel column (8 g, ether:hexane=1:10). The collected fractions were concentrated under reduced pressure. The residue was left to stand for 7 hours under reduced pressure (<4 mmHg) created by a vacuum pump to give 11,15-bis(tbutyldimethylsilyl)prostaglandin $E_2$ methyl ester (41.8 mg; 87%).

TLC: Rf=0.58 (ethyl acetate:hexane=1:5).

IR (liquid film): 1743, 1243, 1000, 964, 927, 828 and 768 cm$^{-1}$.

$^1$H NMR (CDCl$_3$)δ: 0.03 and 0.06 (each s, 12, SiCH$_3$×4), 0.8–1.0 (m, 21, C-CH$_3$×7), 1.2–1.5 (m, 8, $CH_2 \times 4$), 1.6-2.9 (m, 12, $CH_2CO \times 2$, $CH_2C=\times 2$, $CH \times 2$ and $CH_2$), 3.67 (s, 3, $OCH_3$), 4.06 (m, 2, CHO-Si$\times$2), 5.37 (m, 2, vinyl), 5.54 (m, 2, vinyl).

$[\alpha]_D^{21}$: $-52.7°$ (C 1.28, $CH_3OH$).

This compound completely agreed with the 11,15-protected disilyl compound derived from (−)-PGE$_2$.

REFERENTIAL EXAMPLE 2

Synthesis of prostaglandin E$_2$ methyl ester

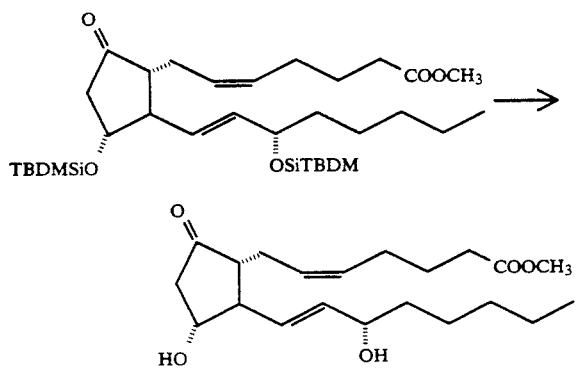

11,15-bis(t-butyldimethylsilyl)prostaglandin E$_2$ methyl ester (40 mg, 0.067 mmole) was dissolved in anhydrous acetonitrile (8 ml), and at 0° C., HF-pyrifine (0.1 ml) was added. The mixture was stirred at 24° C. for 30 minutes. HF-pyridine (0.4 ml) was added further, and the mixture was stirred for 3 hours, and then poured into a saturated aqueous sodium bicarbonate solution (20 ml). The mixture was extracted with ethyl acetate three times (30 ml $\times$ 3). The organic layers were combined, dried over anhydrous sodium sulfate, and concentrated under reduced pressure. Toluene was added to the residue, and the mixture was further concentrated under reduced pressure in order to remove pyridine from the residue. The residue was left to stand for a while under reduced pressure (<4 mmHg) created by a vacuum pump, and then chromatographed on a silica gel column [2 g, ethyl acetate:hexane (1:1)→(1:0) gradient] to give (−)-PGE$_2$ methyl ester (24.1 mg, 98%).

TLC: Rf=0.29 (ethyl acetate:cyclohexane:THF=6:3:1).

IR (liquid film): 3680-3080, 1744 and 970 cm$^{-1}$.

$^1$H NMR (CDCl$_3$)$\delta$: 0.90 (t, 1, J:6.5 Hz, CH$_3$), 1.1-2.9 (m, 20, $CH_2CO \times 2$, $CH_2 \times 5$, $CH_2C=\times 2$, $CH \times 2$), 3.08 (br, 1, OH), 3.66 (s, 3, OCH$_3$), 4.06 (m, 3, CHO $\times$ 2 and OH), 5.34 (m, 1, vinyl), 5.70 (m, 1, vinyl).

$^{13}$C NMR (CDCl$_3$-CCl$_4$)$\delta$: 14.0, 22.6, 24.7, 25.1, 26.6, 31.7, 33.5, 37.3, 46.1, 51.5, 53.7, 54.5, 72.0, 73.0, 126.6, 130.8, 131.5, 136.8, 174.0, 214.1.

$[\alpha]_D^{22}$: $-71.7°$ (C 1.043, CH$_3$OH).

REFERENTIAL EXAMPLE 3

Synthesis of 11,15-bis(t-butyldimethylsilyl)-5,6-prostaglandin F$_{2\alpha}$ methyl ester

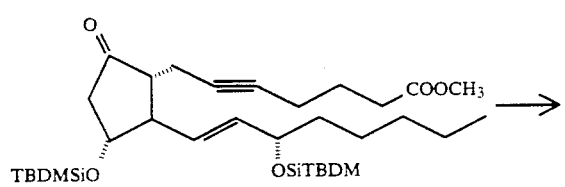

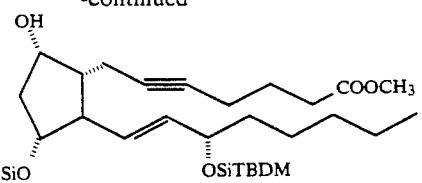

A toluene solution (1 ml) of 11,15-bis(t-butyldimethylsilyl)-5,6-dehydroprostaglandin E$_2$ methyl ester (25.5 mg; 0.043 mmole) was added at −78° C. to a toluene solution (0.192M; 2.24 ml; 0.43 mmole) of diisobutylaluminum hydride (1 equivalent)/2,6-di-t-butyl-4-methylphenol (2 equivalents). The mixture was stirred at −78° C. for 2 hours. The temperature was then elevated, and the mixture was stirred at −25° to −20° C. for 3 hours. A saturated aqueous sodium hydrogen tartrate solution (10 ml) was added, and the mixture was vigorously shaken. It was extracted three times with ethyl acetate (20+10+10 ml) at room temperature. The organic layers were combined, dried over anhydrous sodium sulfate, and concentrated under reduced pressure.

The residue was chromatographed on a silica gel column (5 g, ethyl acetate:hexane=5:1) to give 11,15-bis(t-butyldimethylsilyl)-5,6-dehydroprostaglandin F$_{2\alpha}$ methyl ester (23.5 mg, 92%, a component having low polarity).

TLC: Rf=0.29 (ethyl acetate:hexane=1:5).

IR (liquid film): 3640-3080, 1745, 1247, 1020, 970, 930, 830 and 770 cm$^{-1}$.

$^1$H NMR (CDCl$_3$)$\delta$: 0.02 and 0.05 (each s, 12, SiCH$_3 \times 4$), 0.7-1.0 (m, 21, C—CH$_3 \times 7$), 2.1-3.5 (m, 20, $CH_2CO$, $CH_2 \times 6$, $CH_2C=\times 2$, and CH$\times$2), 3.69 (d, 1, J=8.3 Hz, OH), 3.67 (s, 3, OCH$_3$), 4.00 and 4.24 (br, 3, CHO$\times$3), 5.40 (m, 2, vinyl).

$[\alpha]_D^{21}$: $+0.37°$ (C 0.715, CH$_3$OH).

REFERENTIAL EXAMPLE 4

Synthesis of 11,15-bis(t-butyldimethylsilyl)prostaglandin F$_{2\alpha}$ methyl ester

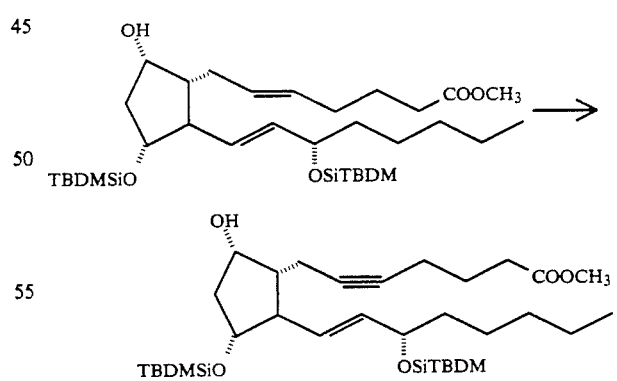

11,15-bis(t-butyldimethylsilyl)-5,6-dehydroprostaglandin F$_{2\alpha}$ methyl ester (28.7 mg; 0.048 mmole) was dissolved in benzene (1 ml), and cyclohexane (1 ml) and Linder catalyst (28.7 mg) were added. The mixture was stirred at 22 to 23.5° C. for 12 hours in an atmosphere of hydrogen. The catalyst was removed by filtration. The filtrate was washed with ethyl acetate. The organic layers were combined and concentrated under reduced pressure.

The concentrate was chromatographed on a silica gel column (6 g, ethyl acetate:hexane:benzene=1:15:2) to give 11,15-bis(t-butyldimethylsilyl)prostaglandin F$_{2\alpha}$ methyl ester (23.2 mg, 81%).

TLC: Rf=0.32 (ethyl acetate:hexane=1:5).

IR (liquid film): 3610–3280, 1745, 1250, 1000, 970, 938, 830 and 770 cm$^{-1}$.

$^1$H NMR (CDCl$_3$)δ: 0.03 and 0.05 (each s, 12, SiCH$_3$×4), 0.8–1.0 (m, 21, C—CH$_3$×7), 1.2–2.4 (m, 20, CH$_2$CO, CH$_2$×6, CH$_2$C=×2, and CH×2), 2.69 (d, 1, J=9.5 Hz, OH), 3.67 (s, 3, OCH$_3$), 4.05 (br, 3, CHO×3), 5.40 (m, 2, vinyl).

[α]$_D^{23}$: +12.3° (C 1.037, CH$_3$OH).

REFERENTIAL EXAMPLE 5

Synthesis of prostaglandin F$_{2\alpha}$ methyl ester

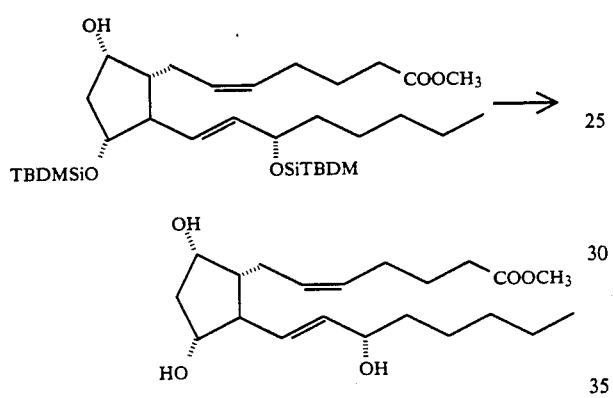

11,15-bis(t-butyldimethylsilyl)prostaglandin F$_{2\alpha}$ methyl ester (21 mg, 0.035 mmole) was dissolved in acetic acid (1 ml), and H$_2$O (0.33 ml) and THF (0.1 ml) were added. The mixture was stirred at 55° C. for 1.5 hours. The mixture was transferred to a large vessel, and toluene was added. The mixture was concentrated under pressure several times to remove acetic acid and H$_2$O. The residue was chromatographed on a silica gel column [3 g, ethyl acetate-hexane (1:1)→(1:0), gradient] to give (+)-PGF$_{2\alpha}$ methyl ester (11 mg, 85%).

TLC: Rf=0.2 (ethyl acetate:cyclohexane:THF=6:3:1)

IR (liquid film): 3640–3040, 1738, 1435, 1160, 1116, 1042, 1020, 968 and 858 cm$^{-1}$.

$^1$H NMR (CDCl$_3$)δ: 0.89 (t, s, J=6.5 Hz, CH$_3$), 1.2–2.4 (m, 20, CH$_2$CO, CH$_2$×6, CH$_2$C=×2, and CH×2), 2.57 (br, 1, OH), 3.29 (br, 1, OH), 3.69 (s, 3, OCH$_3$), 4.03 (brm, 3, CHO×3), 5.3–5.6 (m, 2, vinyl).

$^{13}$C NMR (CDCl$_3$)δ: 14.0, 22.6, 24.8, 25.2, 25.6, 26.6, 31.8, 33.5, 37.3, 43.0, 50.5, 51.6, 55.8, 72.9, 73.0, 78.0, 129.1, 129.6, 132.6, 135.3, 174.3.

[α]$_D^{20}$: +31.4° (C 0.423, CH$_3$OH).

The spectral data (IR, $^1$HNMR, $^{13}$CNMR, TLC) of the product completely agreed with those of (+)-PGF$_{2\alpha}$ methyl ester derived from (+)-PGF$_{2\alpha}$.

What is claimed is:

1. A process for producing a 2,3-disubstituted-4-substituted cyclopentanone represented by the formula

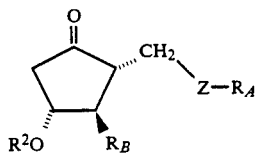

R$^2$ represents a tri(C$_1$-C$_7$) hydrocarbon silyl group or R$^2$O represents an acetal linkage, R$_B$ represents a substituted or unsubstituted C$_2$-C$_{10}$ alkyl or alkenyl group, Z represents an ethylene, trans-vinylene, or cis-vinylene, group, and R$_A$ represents a substituted or unsubstituted C$_1$-C$_6$ alkyl group, an enantiomorph thereof, or a mixture of these in an arbitrary ratio, which comprises (A) subjecting a 4-substituted-2-cyclopentenone represented by the following formula

wherein R$^2$ is as defined above,
an enantiomorph thereof, or a mixture of these in an arbitrary ratio, and an organocopper compound formed from an organolithium compound represented by the following formula $$R_B—Li \qquad (2)$$

wherein R$_B$ is as defined above,
and a copper compound represented by the following formula $$Cu—Q \qquad (3)$$

wherein Q represents a halogen atom, a cyano group, a phenylthio group or a 1-pentynyl group, to conjugate addition-reaction, and thereafter, (B) reacting the resulting enolate intermediate with a halide represented by the following formula $$X—CH_2—Z—R_A \qquad (5)$$

wherein Z and R$_A$ are as defined above, and X represents a halogen atom or a tosyl group, in the presence of an organotin compound represented by the following formula $$R_3BnY \qquad (4)$$

wherein R's are identical or different and each represents a phenyl group or a halogen atom provided that two or three R's cannot be halogen atoms at the same time, and Y represents a halogen atom.

2. The process of claim 1 wherein in the organolithium compound represented by formula (2), R$_B$ is a substituted or unsubstituted C$_2$-C$_{10}$ alkenyl group, and the substituent on the alkenyl group is a C$_1$-C$_4$ alkyl group, a C$_3$-C$_7$ cycloalkyl group, a C$_2$-C$_4$ alkynyl group, a phenyl group, a phenoxy group, a C$_1$-C$_4$ alkoxy group, or the group OR$^2$ in which R$^2$ is as defined above, provided that the phenyl and phenoxy groups may further be substituted by fluoro, methyl, trifluoromethyl or trifluoromethoxy.

3. The process of claim 1 wherein in the organolithium compound represented by formula (2), $R_B$ is a substituted or unsubstituted $C_2$-$C_{10}$ alkyl group, and the substituent on the alkyl group is a $C_3$-$C_7$ cycloalkyl group, a vinyl group, a $C_2$-$C_4$ alkynyl group, a phenyl group, a phenoxy group, a $C_1$-$C_4$ alkoxy group or the group $OR^2$ in which $R^2$ is as defined above, provided that the phenyl and phenoxy groups may further be substituted by fluoro, methyl, trifluoromethyl or trifluoromethoxy.

4. The process of claim 1 wherein the organolithium compound of formula (2) is represented by the following formula

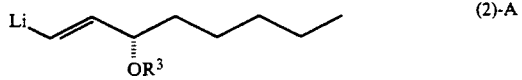 (2)-A wherein $R^3$ is a tri($C_1$-$C_7$)hydrocarbon silyl group or $OR^3$ represents an acetal linkage.

5. The process of claim 1 wherein in the organotin compound represented by formula (4), R's are identical or different and each represents a phenyl group.

6. The process of claim 1 wherein the halide represented by formula (5) is represented by the following formula $$X—CH_2—(CH_2)_n—COOR^1 \quad (5)-1$$

wherein X is as defined above in formula (5), $R^1$ represents a $C_1$-$C_{10}$ alkyl group, a substituted or unsubstituted phenyl group, a substituted or unsubstituted $C_3$-$C_7$ cycloalkyl group or a substituted or unsubstituted phenyl ($C_1$-$C_2$)alkyl group, and n is an integer of 3 to 8.

7. The process of claim 1 wherein the halide of formula (5) is an iodide.

8. The process of claim 1 wherein the conjugate addition reaction in step (A) is carried out in the presence of a trivalent organophosphorus compound.

9. The process of claim 1 wherein the enolate intermediate formed by the conjugate addition reaction in step (A) is reacted with the halide (5) in the presence of the organotin compound (4) in step (B) in an aprotic polar solvent.

10. The process of claim 1 wherein $R^2$ represents t-butyl-dimethylsilyl.

11. The process of claim 8 wherein the organophosphorus compound is tributylphosphine or hexamethylphosphoric triamide.

12. The process of claim 8 wherein the conjugate addition reaction in step (A) is carried out at −78° to 0° C. in an aprotic polar organic medium using 0.5 to 2.0 moles of the organocopper compound per mole of the 4-substituted-2-cyclopentenone.

13. The process of claim 9 wherein the enolate intermediate formed by the conjugate addition reaction in step (A) is reacted with 0.8 to 5.0 moles of the halide (5) in the presence of 0.8 to 1.5 moles of the organotin compound (4) each per mole of the starting 4-substituted-2-cyclopentenone at −100° to 0° C.

14. The process of claim 1, wherein the organotin compound is $Ph_3SnCl$.

15. A process for producing a 2,3-disubstituted-4-substituted cyclopentanone represented by the formula

 (6)

wherein $R^2$ represents a tri($C_1$-$C_7$-hydrocarbon silyl group or $R^2O$ represents an acetal linkage, $R_B$ represents a substituted or unsubstituted $C_2$-$C_{10}$ alkyl or alkenyl group, Z represents an ethylene, transvinylene or cis-vinylene group, and $R_A$ represents a substituted or unsubstituted $C_1$-$C_6$ alkyl group, or —$CH_2$—Z—$R_A$ represents —$CH_2$—$(CH_2)_n$—$COOR^1$ wherein $R^1$ represents a $C_1$-$C_{10}$ alkyl group, a substituted or unsubstituted phenyl group, a substituted or unsubstituted $C_3$-$C_7$ cycloalkyl group or a substituted or unsubstituted phenyl ($C_1$-$C_2$) alkyl group, and n is an integer of 3 to 8, an enantiomorph thereof, or a mixture of these in an arbitrary ratio, which comprises (A) subjecting a 4-substituted-2-cyclopentanone represented by the following formula

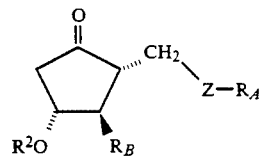 (1)

wherein $R^2$ is as defined above, an enantiomorph thereof, or a mixture of these in an arbitrary ratio, and an organocopper compound formed from an organolithium compound represented by the following formula $$R_B—Li \quad (2)$$

wherein $R_B$ is as defined above, and a copper compound represented by the following formula $$Cu—Q \quad (3)$$

wherein Q represents a halogen atom, a cyano group, a phenylthio group or a 1-pentynyl group, to conjugate addition-reaction, and thereafter, (B) reacting the resulting enolate intermediate with a halide represented by the following formula $$X—CH_2—Z—R_A \quad (5)$$

wherein Z and $R_A$ are as defined above, and X represents a halogen atom or a tosyl group, in the presence of an organotin compound represented by the following formula $$R_3SnY \quad (4)$$

wherein R's are identical or different and each represents a phenyl group or a halogen atom provided that two or three R's cannot be halogen atoms at the same time, and Y represents a halogen atom.

16. The process of claim 15, wherein the organotin compound is $Ph_3SnCl$.

17. A process for producing a 2,3-disubstituted-4-substituted cyclopentanone represented by the formula

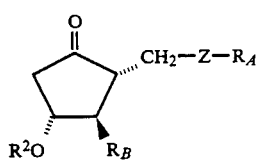  (6)

wherein $R^2$ represents a tri($C_1$-$C_7$)-hydrocarbon silyl group or $R^2O$ represents an acetal linkage, $R_B$ represents a substituted or unsubstituted $C_2$-$C_{10}$ alkyl or alkenyl group, Z represents an ethynylene, transvinylene or cis-vinylene group, and $R_A$ represents —$(CH_2)_{n-2}$COO$R^1$ wherein $^1$ represents a $C_1$-$C_{10}$ alkyl group, a substituted or unsubstituted phenyl group, a substituted or unsubstituted $C_3$-$C_7$ cycloalkyl group or a substituted or unsubstituted phenyl ($C_1$-$C_2$) alkyl group, and n is an integer of 3 to 8, an enantiomorph thereof, or a mixture of these in an arbitrary ratio, which comprises (A) subjecting a 4-substituted-2-cyclopentanone represented by the following formula

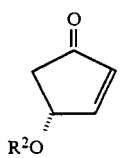  (1)

wherein $R^2$ is as defined above, an enantiomorph thereof, or a mixture of these in an arbitrary ratio, and an organocopper compound formed from an organolithium compound represented by the following formula $$R_B-Li \qquad (2)$$

wherein $R_B$ is as defined above, and a copper compound represented by the following formula $$Cu-Q \qquad (3)$$

wherein Q represents a halogen atom, a cyano group, a phenylthio group or a 1-pentynyl group, to conjugate addition-reaction;

and thereafter, (B) reacting the resulting enolate intermediate with a halide represented by the following formula $$X-CH_2-Z-R_A \qquad (5)$$

wherein Z and $R_A$ are as defined above, and X represents a halogen atom or a tosyl group, in the presence of an organotin compound represented by the following formula $$R_3SnY \qquad (4)$$

wherein R's are identical or different and each represents a phenyl group or a halogen atom provided that two or three R's cannot be halogen atoms at the same time, and Y represents a halogen atom.

18. The process of claim 17, wherein the organotin compound is $Ph_3SnCl$.

* * * * *